(12) United States Patent
Zaidat

(10) Patent No.: US 10,265,085 B2
(45) Date of Patent: Apr. 23, 2019

(54) SYSTEM AND DEVICE FOR ENGULFING THROMBI

(71) Applicant: Osama O. Zaidat, Lambertville, MI (US)

(72) Inventor: Osama O. Zaidat, Lambertville, MI (US)

(*) Notice: Subject to any disclaimer, the term of this patent is extended or adjusted under 35 U.S.C. 154(b) by 0 days.

(21) Appl. No.: 15/802,235

(22) Filed: Nov. 2, 2017

(65) Prior Publication Data

US 2018/0132876 A1 May 17, 2018

Related U.S. Application Data

(60) Provisional application No. 62/422,870, filed on Nov. 16, 2016.

(51) Int. Cl.
| | |
|---|---|
| *A61B 17/22* | (2006.01) |
| *A61M 25/10* | (2013.01) |
| *A61B 17/12* | (2006.01) |
| *A61B 17/3207* | (2006.01) |
| *A61B 17/221* | (2006.01) |

(52) U.S. Cl.
CPC .... *A61B 17/22032* (2013.01); *A61B 17/1215* (2013.01); *A61B 17/221* (2013.01); *A61B 17/320725* (2013.01); *A61M 25/10181* (2013.11); *A61B 2017/22034* (2013.01); *A61B 2017/22035* (2013.01); *A61B 2017/22079* (2013.01)

(58) Field of Classification Search
CPC ............ A61B 17/221; A61B 17/32056; A61B 2017/2212
See application file for complete search history.

(56) References Cited

U.S. PATENT DOCUMENTS

| | | | | |
|---|---|---|---|---|
| 6,371,970 | B1* | 4/2002 | Khosravi | A61F 2/01 606/194 |
| 7,094,249 | B1* | 8/2006 | Broome | A61B 17/221 606/200 |
| 8,529,596 | B2* | 9/2013 | Grandfield | A61B 17/320725 606/127 |
| 2013/0079796 | A1* | 3/2013 | Slee | A61B 17/221 606/127 |
| 2013/0268064 | A1* | 10/2013 | Duffy | A61F 2/2436 623/2.11 |

(Continued)

OTHER PUBLICATIONS

Search Report for International Application No. PCT/US2017/059759, dated Mar. 1, 2018, 10 pages.

*Primary Examiner* — Julie A Szpira
(74) *Attorney, Agent, or Firm* — Foley & Lardner LLP

(57) ABSTRACT

A system for removing a thrombus from a blood vessel includes a stent retriever, a catheter configured to receive the stent retriever in a collapsed configuration, wherein the stent retriever is movable relative to the catheter, a sheath having a tubular body and defining a distal opening and a proximal opening, and a wire coupled to the stent retriever for positioning the stent retriever. The wire extends through the proximal opening and the distal opening of the sheath. The stent retriever is moveable relative to the sheath, and the distal opening of the sheath is sized to allow the stent retriever to be withdrawn into the sheath without substantially compressing the stent retriever.

20 Claims, 18 Drawing Sheets

(56) References Cited

U.S. PATENT DOCUMENTS

| | | | |
|---|---|---|---|
| 2014/0121672 A1* | 5/2014 | Folk | A61B 17/221 606/127 |
| 2014/0155908 A1* | 6/2014 | Rosenbluth | A61B 17/320725 606/127 |
| 2016/0015403 A1* | 1/2016 | Nguyen | A61B 17/221 606/127 |
| 2016/0192957 A1* | 7/2016 | Okada | A61B 17/221 606/127 |
| 2017/0086864 A1* | 3/2017 | Greenhalgh | A61B 17/221 |
| 2017/0303939 A1* | 10/2017 | Greenhalgh | A61B 17/22 |

* cited by examiner

SYSTEM AND DEVICE FOR ENGULFING THROMBI

CROSS-REFERENCE TO RELATED APPLICATION

This application claims the benefit of and priority to U.S. Application No. 62/422,870 filed on Nov. 16, 2016, which is incorporated herein by reference in its entirety.

BACKGROUND

Blood flow through the circulatory system can be restricted when a thrombus (blood clot) or foreign body develops inside a blood vessel or occlusive thromboembolism occurs. A thrombus is generally formed from platelets and fibrin to prevent loss of blood due to an injury to the blood vessel. Serious complications can occur if a thrombus grows too large and obstructs too much of the blood vessel. The thrombus may also break loose, forming an embolus that can lodge in another part of the body, obstructing blood flow and potentially causing irreversible harm to organs or death.

Ischemia is a reduction in blood flow to an organ or tissue, causing damage due to a lack of sufficient oxygen or fuel being delivered to the cells. One type of stroke (an ischemic stroke) occurs when a cerebral vessel is obstructed (such as by a thrombus or an embolus), reducing blood flow to a specific region of the brain. A blockage of this type can quickly lead to irreversible damage to brain tissue and death. It can be seen, therefore, that there is a great need for effective treatment options to remove blood clots to increase the blood flow to organs such as the brain while minimizing the fragmentation of the thrombus during removal.

A device known as a stent retriever may be utilized to capture and remove a thrombus from a blood vessel. The stent retriever is introduced into the blood vessel with a catheter. The stent retriever is the inserted into the thrombus and deployed. Upon deployment, the stent retriever expands to engage and capture the thrombus. The stent, along with the thrombus, is removed from the vessel, allowing blood to begin flowing again through the vessel. The stent retriever is engulfed in to a large bore catheter so that the thrombus captured and removed by the stent retriever en bloc without fragmentation.

SUMMARY OF THE INVENTION

One embodiment of the invention relates to a system for removing a thrombus from a blood vessel. The system includes a stent retriever; a first catheter, a sheath, and a wire coupled to the stent retriever. The first catheter is configured to receive the stent retriever in a collapsed configuration. The first catheter includes a tubular body and defining a distal opening and a proximal opening. The wire extends through the proximal opening and the distal opening of the sheath. The stent retriever is moveable relative to the sheath. The distal opening is sized to allow the stent retriever to be withdrawn into the sheath without substantially compressing the stent retriever and the proximal opening is sized to prevent the passage of the removed stent retriever.

Another embodiment of the invention relates to a system for removing a thrombus from a blood vessel. The system includes a stent retriever; a first catheter, and a guide catheter configured to receive the catheter. The first catheter is configured to receive the stent retriever in a collapsed configuration. The guide catheter includes an expandable distal portion. The diameter of the expandable distal portion is able to vary between a minimum diameter in which the expandable distal portion comprises a generally cylindrical shape and a maximum diameter in which the expandable distal portion comprises a generally non-cylindrical shape in order to occlude the downstream flow to prevent escape of the clot or foreign body from the retrieval device. The stent retriever is moveable relative to the guide catheter. When the distal portion is expanded to the maximum diameter, the distal portion defines an opening that is sized to allow the stent retriever to be withdrawn into the sheath without substantially compressing the stent retriever.

Yet another embodiment of the invention relates to a stent retriever for removing a thrombus from a blood vessel. The stent retriever includes a plurality of raised portions, and a plurality of lateral recesses defined between the raised portions. The stent retriever is expandable from a compressed configuration to an expanded configuration. The plurality of lateral recesses receive portions of the thrombus when the stent retriever is in the expanded configuration. The stent retriever is structured to capture and remove the thrombus or foreign body in one piece without fragmentation.

The invention is capable of other embodiments and of being practiced or being carried out in various ways. Alternative exemplary embodiments relate to other features and combinations of features as may be generally recited in the claims.

BRIEF DESCRIPTION OF THE DRAWINGS

These and other features, aspects and advantages of the present invention will become apparent from the following description, appended claims, and the accompanying exemplary embodiments shown in the drawings, which are briefly described below.

DETAILED DESCRIPTION

Catheter systems and methods are used to remove a thrombus from a blood vessel, such as a cerebral artery, according to several exemplary embodiments. The catheter system and methods use a stent device which is deployed to capture the thrombus such that the thrombus is removed from the blood vessel with the removal of the stent device. In some embodiments, the stent device and the thrombus are surrounded by a sheath or other body to reduce fragmentation of the thrombus and the formation of emboli.

Figures 1A, 1B:
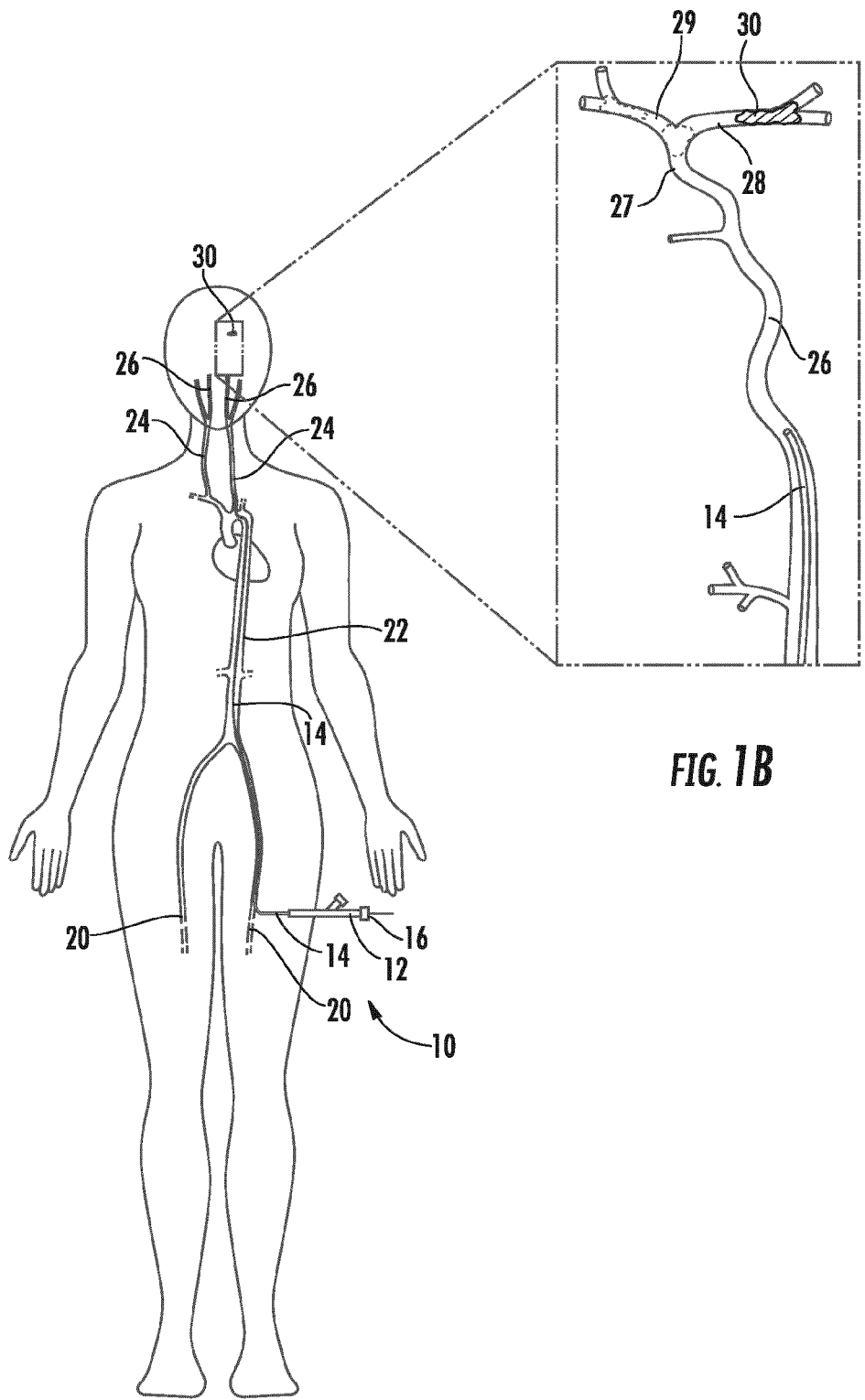
FIG. 1A depicts a catheter device introduced into a patient's vascular system.
FIG. 1B is an enlarged view of the catheter device of FIG. 1A introduced into a patient's cerebral vascular system.

Referring to FIGS. 1A-1B, the catheter device 10 is shown being introduced into a patient's vascular system. The catheter device 10 includes a base 12 and a delivery or guide catheter 14 that is introduced into the body. The base 12 (e.g., manifold) includes a rotating hemostatic valve (RHV) 16 through which the guide catheter 14 extends and allows medical personnel to manipulate the guide catheter 14. The guide catheter 14 provides a conduit through which various instruments may be deployed to a desired location within the patient's body, as described in more detail below.

For a thrombus 30 located in the brain, the catheter device 10 is inserted into the femoral artery 20 through an incision in the thigh. The guide catheter 14 is generally advanced through the femoral artery 20 to the aorta 22, through the aorta 22 to a common carotid artery 24 (e.g., the left or right common carotid artery). According to the illustrated scenario, the thrombus 30 is located in the middle cerebral artery 28. The guide catheter is therefore advanced through the common carotid artery 24 to the internal carotid artery 26. While a thrombus commonly forms in the middle cerebral artery 28, it will be appreciated that the catheter device 10 may be utilized to remove a thrombus located elsewhere, such as at the terminus 27 of the internal carotid artery, in the anterior cerebral artery 29, or in another area of the patient's vascular system.

Figure 2:
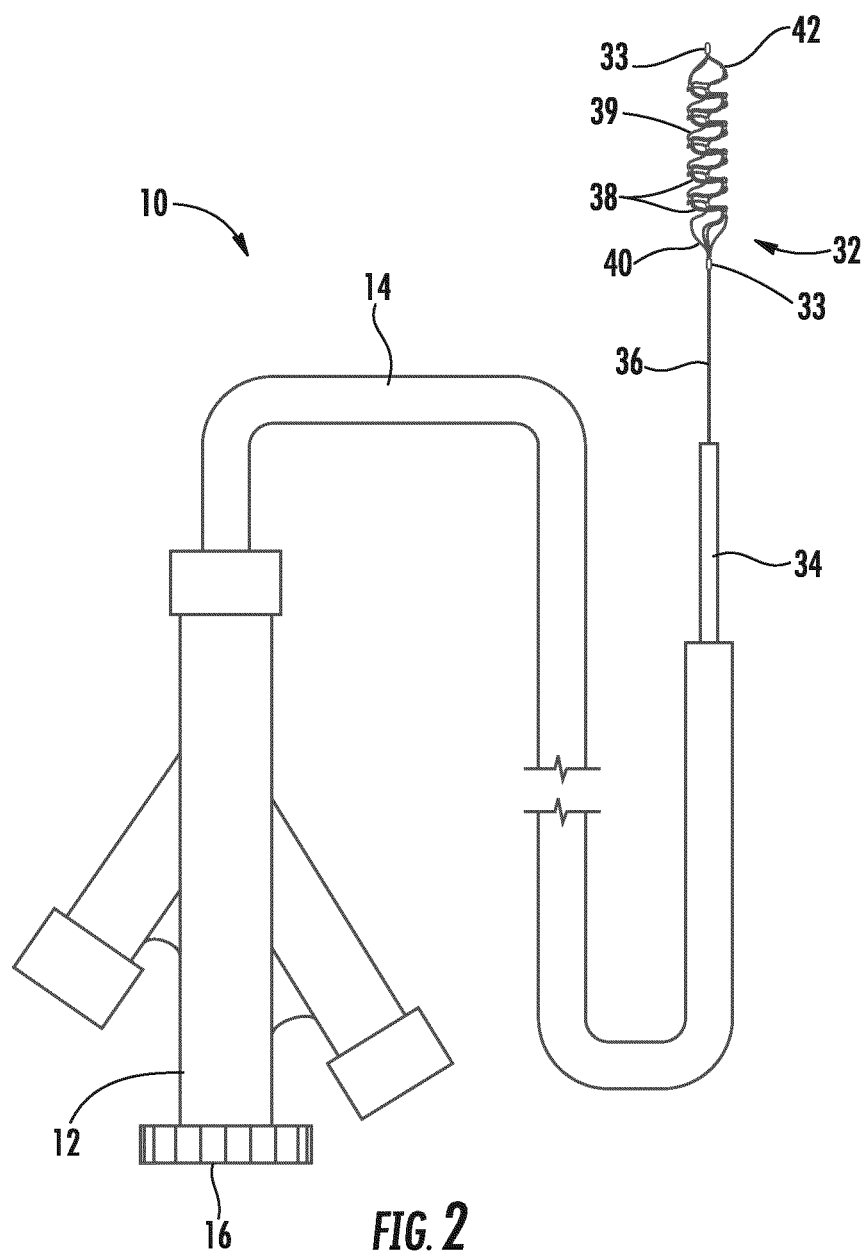
FIG. 2 is a side view of a catheter device, according to an exemplary embodiment.

Referring now to FIG. 2, the catheter device 10 is shown in more detail. The catheter device 10 includes a stent retriever 32. The stent retriever 32 is advanced to the location of the thrombus 30 in a contracted configuration within a microcatheter 34 via a push wire 36. According to an exemplary embodiment, the push wire 36 has a diameter of approximately 0.14 inch. In other embodiments, a larger or smaller diameter push wire may be used. Upon deployment, the stent retriever 32 expands, compressing the thrombus against the walls of the blood vessel and captures the thrombus 30. The stent retriever 32 is then retracted, removing the thrombus 30 in the process.

Figure 3A:
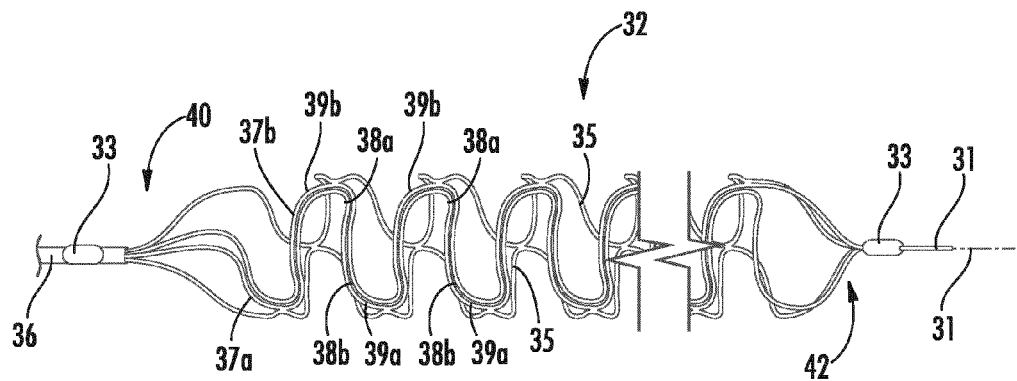
FIG. 3A is a perspective view of a stent retriever, according to an exemplary embodiment.
Figure 3B:
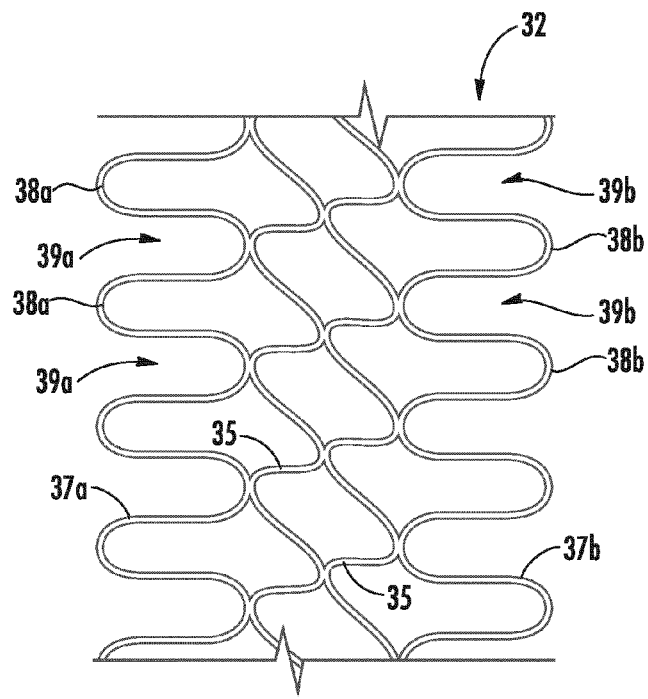
FIG. 3B is a side view of a stent retriever according to an exemplary embodiment, shown opened from a cylindrical form.

Referring to FIGS. 3A and 3B, the stent retriever 32 is shown in more detail. FIG. 3A is an illustration of a side view of the stent retriever 32 and FIG. 3B is an illustration of an opened, substantially flat configuration of the stent retriever 32. The substantially cylindrical stent retriever 32 of FIG. 3A is formed by bringing together the two side edges of the opened mesh sheet shown in FIG. 3B. According to an exemplary embodiment, the stent retriever 32 is formed from a suitable biocompatible metal or alloy (e.g., platinum, stainless steel, nickel-titanium alloy, etc.) or a suitable biocompatible polymer. The stent retriever 32 may be self-expandable or may be expanded with another device, such as an inflatable balloon. All or part of the stent retriever 32 may be coated or covered with a radiopaque material, such as platinum to allow for visualization of the stent retriever 32. According to one exemplary embodiment, the stent retriever 32 includes radiopaque markers 33 at a proximal 40 end and a distal end 42 to aid in the positioning of the stent retriever 32 relative to the thrombus 30.

The stent retriever 32 is an open, generally cylindrical body that includes a multitude of protrusions 38 (e.g., fingers, projections, arms, etc.). According to one exemplary embodiment, a row of first protrusions 38a are formed from a first undulating wire member 37a. The protrusions 38a are formed as U-shaped members that are oriented laterally (e.g., generally perpendicular to a longitudinal axis 31 of the stent retriever 32). Recesses 39a (e.g., hollows, depressions, etc.) are formed between each of the protrusions 38a. The recesses 39a are U-shaped similar to the protrusions 38a. A row of second protrusions 38b are formed from a second undulating wire member 37b. The protrusions 38b are formed as U-shaped members that are oriented laterally (e.g., generally perpendicular to the longitudinal axis 31 of the stent retriever 32). Recesses 39b (e.g., hollows, depressions, etc.) are formed between each of the protrusions 38b. The recesses 39b are U-shaped similar to the protrusions 38b. The protrusions 38a and 38b are disposed in an interlocking (e.g., interdigitated) arrangement such that the protrusions 38a are received in the recesses 39b and the protrusions 38b are received in the recesses 39a to form the cylindrical stent retriever, as shown in FIG. 3A. This interdigitated arrangement provides an efficient grab of the thrombus, so that the thrombus can be captured as one piece. The interdigitated arrangement further prevents fragmentation of the thrombus while the thrombus are captured by the stent retriever 32 and moving along with the stent retriever 32.

Figure 3C:
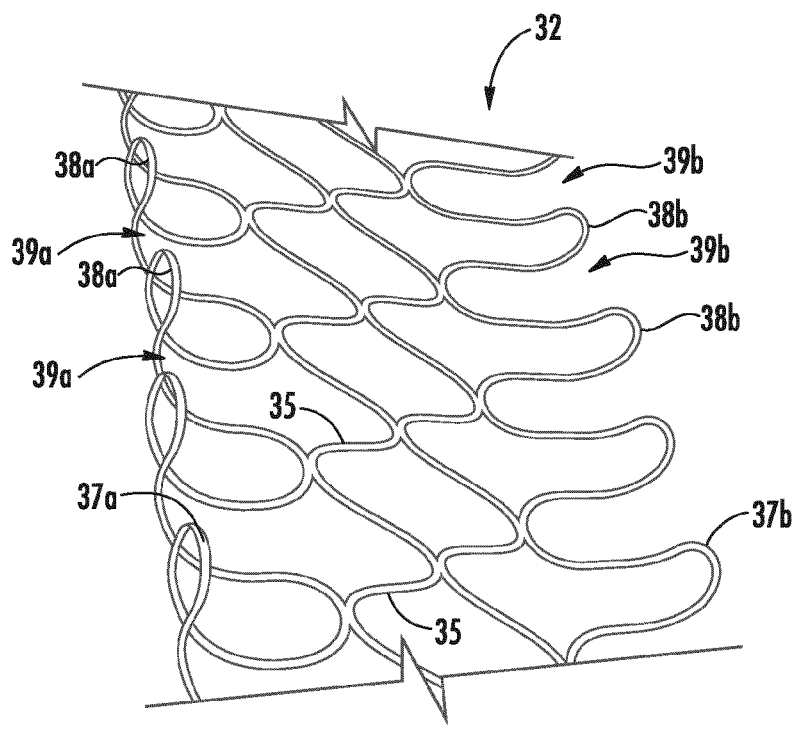
FIG. 3C is a side view of a stent retriever according to an exemplary embodiment, shown opened from a cylindrical form.
Figure 3D:
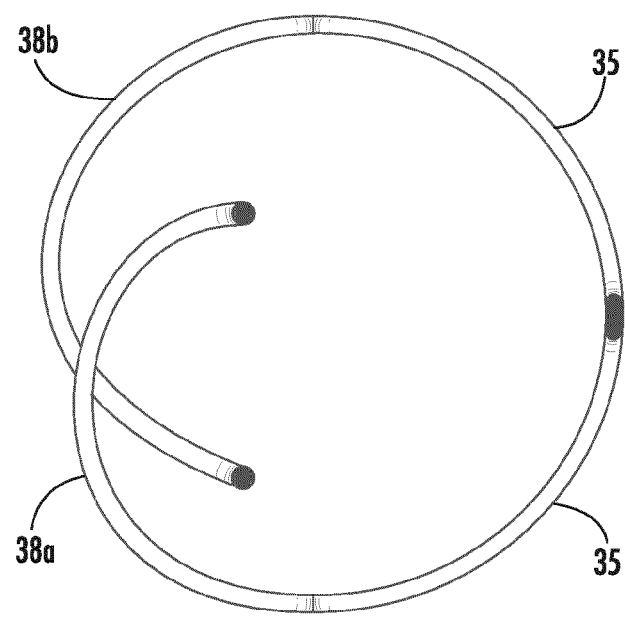
FIG. 3D is a cross-section view of the stent retriever of FIG. 3C in a cylindrical form.

In some embodiments, as shown in FIGS. 3C-3D, the protrusions 38 may comprise a radius of curvature or be otherwise bent at an angle. FIG. 3C is an illustration of an opened, substantially flattened configuration of the stent retriever 32 but for the curved protrusions, such that the sheet forming the cylindrical stent is not entirely planar. FIG. 3D depicts an end view of the stent retriever formed by the sheet of FIG. 3C. In this embodiment, protrusions 38a and 38b are curved such that when the cylindrical body is formed, the protrusions extend into the bore of the cylinder, as shown in the end view of FIG. 3D. Therefore, when the stent retriever 32 is advanced into the thrombus 30 and expanded, the protrusions 38b anchor the thrombus 30 to the stent retriever 32. In the embodiment shown in FIG. 3C, protrusions 38a are curved in more drastically than protrusions 38b. In some embodiments, the protrusions extend at an angle relative to the plane of the connecting members 35 (described below). In some embodiments, the protrusions 38 may all comprise the same curvature or inward angle. In yet further embodiments, the protrusions 38 may have varying degrees of curvature or angle along the length of the stent retriever 32. In some embodiments, all of the protrusions 38 are curved or angled in some way. In other embodiments, at least one, but not all, of the protrusions 38 comprise a curve or extend at an angle.

The wire members 37a and 37b are coupled to each other with connecting members 35. According to an exemplary embodiment, the connecting members 35 are undulating (e.g., sinusoidal) wire members that are coupled to the portions of the wire members 37a and 37b forming the recesses 39a and 39b. In other embodiments, the connecting members may be otherwise configured. For example, in another embodiment, the wire members 37a and 37b may be coupled to each other with a multitude of linear connecting members that extend laterally around the outer circumference of the stent retriever 30 between the wire members 37a and 37b. In some embodiments, the connecting members 35 are fixed to the wire members 37a and 37b. In some embodiments, the connecting members 35 and the wire members 37a and 37b may be interwoven (e.g., twisted together) such that the wire members slide relative to each other as the stent retriever 32 expands or compresses in diameter. The distal end 42 of the stent retriever 32 may include a tip 41. In one embodiment, the tip 41 is a 3 mm platinum wire. In some embodiments, the distal end 42 of the stent retriever may include additional wire members (e.g., a mesh cap) to locally increase the mesh density of the stent retriever 32 and reduce the likelihood that a portion of the thrombus 30 will escape the stent retriever 32 as it is withdrawn.

The protrusions 38 and the recesses 39 facilitate the capturing of the thrombus 30 by the stent retriever 32 and minimize the likelihood of incomplete capturing of the thrombus that could result in fragmentation and the formation of secondary strokes resulting from of embolisms. According to an exemplary embodiment, the stent retriever has a maximum diameter of between 1.5 mm and 10 mm when fully expanded. According to an exemplary embodiment, the stent retriever 32 has a length of between 10-60 mm. According to some embodiments, the length of the stent retriever 32 is customized according to the size of the thrombus. According to an exemplary embodiment, the stent retriever 32 includes multiple protrusions 38. The opening of each of the fully expanded U-shaped protrusions may have a size from 1 mm to 3 mm. According to an exemplary embodiment, the diameter of the stent retriever 32 and the size of the protrusions 38 remain generally constant along the length of the stent retriever 32. In other embodiments, as described in more detail below with regards to FIGS. 11-15, the geometry of the stent retriever may vary along the length of the stent retriever.

It should be noted that the physical dimensions and configurations of the stent retriever 32 described above are exemplary only. In other embodiments, the length, diameter, profile, mesh density, or other physical parameter of the stent retriever 32 may be varied based on the location and characteristics of the thrombus 30 to be removed.

Figure 4A:
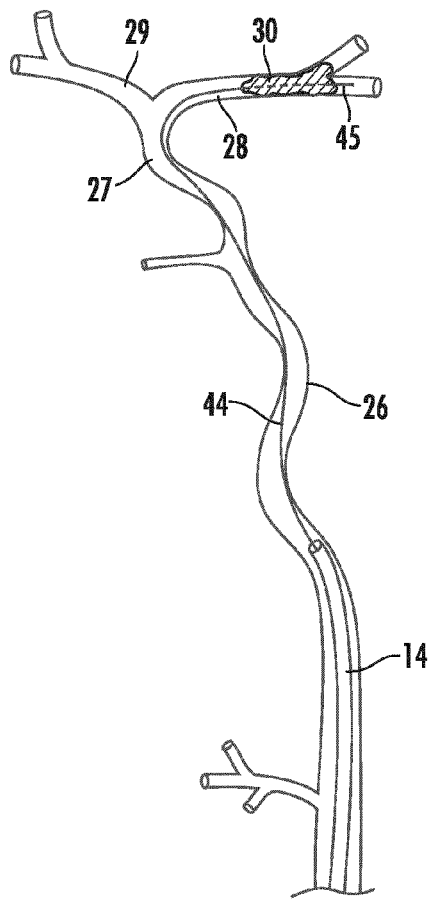
FIGS. 4A-4D depict the catheter device of FIG. 2 being used to remove a thrombus, according to an exemplary embodiment.

Referring now to FIGS. 4A-4D, the catheter device 10 including the stent retriever 32 is shown being used to remove the thrombus 30, according to an exemplary embodiment. As shown in FIG. 4A, the guide catheter 14 is advanced through the patient's vascular system to a position below (e.g., upstream) from the thrombus 30. The guide catheter 14 may be advanced along a guidewire. According to an exemplary embodiment, the guide catheter 14 is advanced along a 0.35" diameter guidewire to the desired location. A microwire 44 is advanced to the thrombus 30 and pierces the thrombus 30 such that a distal end 45 of the microwire 44 is advanced beyond the thrombus 30. According to an exemplary embodiment, the microwire 44 has a diameter of 0.14", however, in other embodiments, a larger or smaller diameter microwire may be used.

Figure 4B:
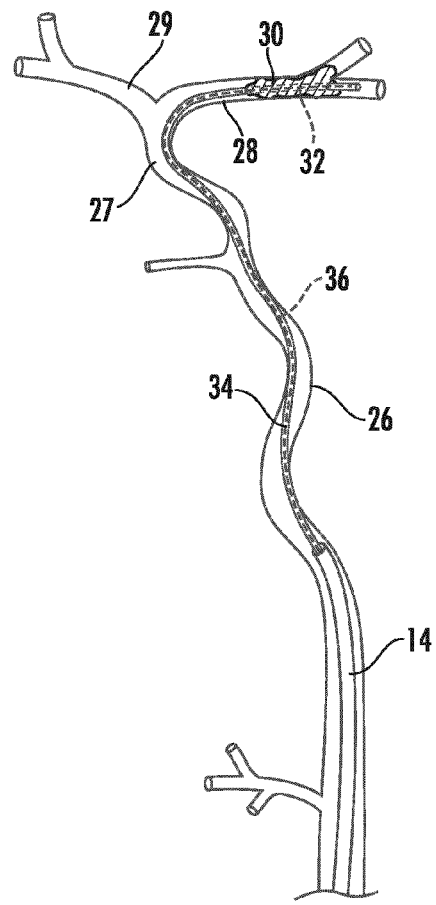

Referring to FIG. 4B, the micro-catheter 34 is advanced along the micro-wire 44 to pass though the thrombus 30. According to an exemplary embodiment, the micro-catheter 34 has an inside diameter of between 0.12 mm and 0.32 mm, however, in other embodiments, a larger or smaller diameter micro-catheter may be used to accommodate the diameter of the microwire 44 and the stent retriever 32. With the micro-catheter 34 in place, the micro-wire 44 is retracted and the stent retriever 32, in a collapsed configuration, is fed through the micro-catheter 34 via the push wire 36 until it passes through the thrombus 30 to a point distal to the thrombus 30. In some embodiments, the stent retriever 32 is positioned with the aid of the radiopaque markers 33.

Figure 4C:
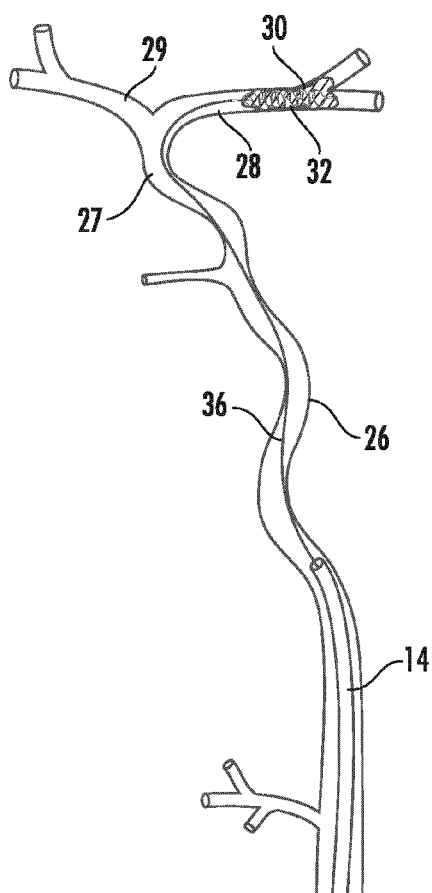

Referring to FIG. 4C, the stent retriever 32 is held stationary by fixing the push wire 36 at the base 12 of the catheter device 10. The microcatheter 34 is retracted to unsheathe the stent retriever 32. The stent retriever 32 expands to envelop the thrombus 30. According to an exemplary embodiment, the stent retriever 32 is a self-expanding body, however, according to other embodiments, the stent retriever 32 may be otherwise expanded. For example, the stent retriever may be expanded with a balloon catheter or similar device.

Figure 4D:
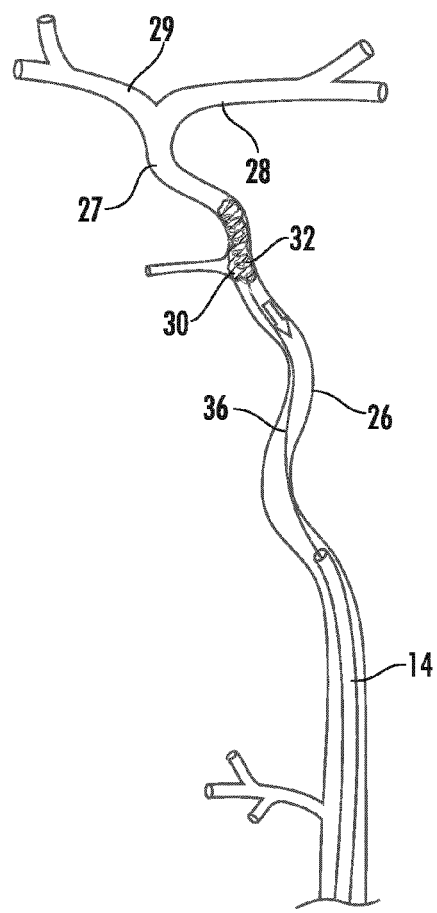

Referring to FIG. 4D, the push wire 36 is released and the stent retriever 32 is withdrawn, removing the thrombus 30 in the process. In one embodiment, the stent retriever 32 and the removed thrombus 30 are retracted back into the guide catheter 14, which is then withdrawn back through the carotid artery 24, the aorta 22, and the femoral artery 20.

Figure 5A:
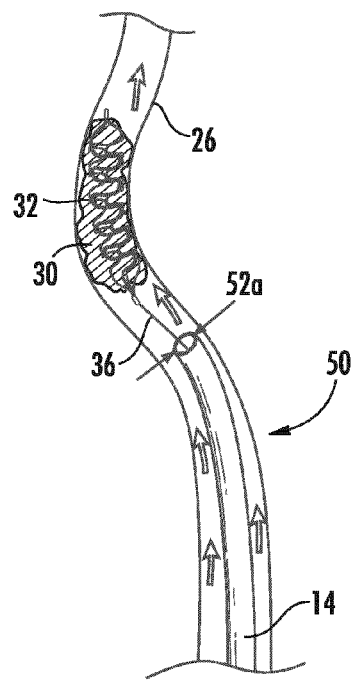
FIGS. 5A-5C depict a catheter device including a catheter with a dynamic distal portion being used to remove a thrombus, according to an exemplary embodiment.
Figure 5B:
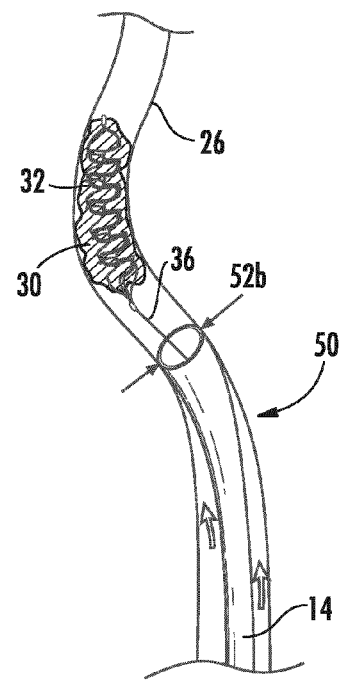
Figure 5C:
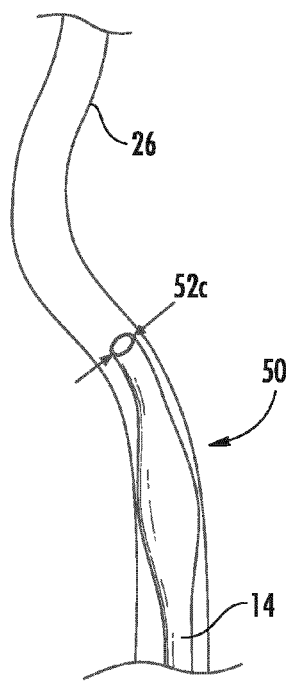

Referring now to FIGS. 5A-5C, in one embodiment, the guide catheter 14 of the catheter device 10 is a dynamic, expandable body having a distal portion 50 that can be expanded and contracted to vary the outlet diameter 52 of the guide catheter 14. For example, in a default configuration, as shown in FIG. 5A, the distal portion 50 of the guide catheter 14 has a first outlet diameter 52a that is less than the outer diameter of the stent retriever 32 and a second or expanded diameter 52b that is greater than the outer diameter of the stent retriever 32, as shown in FIG. 5B. At some point between the deployment of the stent retriever 32 at the location of the thrombus 30 and the retraction of the stent retriever 32, the position of the guide catheter 14 may be constrained and the distal portion 50 of the guide catheter 14 may be expanded to the second outlet diameter 52b. When expanded to the second outlet diameter 52b, the distal portion 50 of the guide catheter 14 forms a funnel-shaped body that facilitates the retraction of the stent retriever 32 and the removed thrombus 30 into the guide catheter 14. In some embodiments, the second diameter 52b is equal to the inner diameter of the blood vessel (e.g., the internal carotid artery 26) in which the distal portion 50 of the guide catheter 14 is disposed. The distal portion 50 of the guide catheter 14 occludes the blood vessel and temporarily prevents the flow of blood past the stent retriever 32 as the thrombus 30 is being retracted towards the guide catheter 14, minimizing the likelihood of fragmentation of the thrombus 30. The distal portion 50 of the guide catheter 14 has a sufficient rigidity to resist the fluid force of the blood flow and maintain the funnel-shaped profile of the distal portion 50 when expanded to the second outlet diameter 52b. As shown in FIG. 5C, after the stent retriever 32 and the removed thrombus 30 have been retracted into the guide catheter 14, the distal portion 50 may be contracted again to a third outlet diameter 52c that is less than the outer diameter of the stent retriever 32. In this configuration, the distal portion 50 envelops the stent retriever 32 and the removed thrombus 30 as they are removed from the patient. In some embodiments, the third outlet diameter 52c is approximately equal to the first outlet diameter 52a.

The distal portion 50 of the guide catheter 14 may be expanded and contracted by various means to vary the outlet diameter 52. For example, according to one exemplary embodiment, the distal portion 50 is expanded and contracted by torque mechanisms, string mechanisms, or spring mechanisms.

Figure 6:
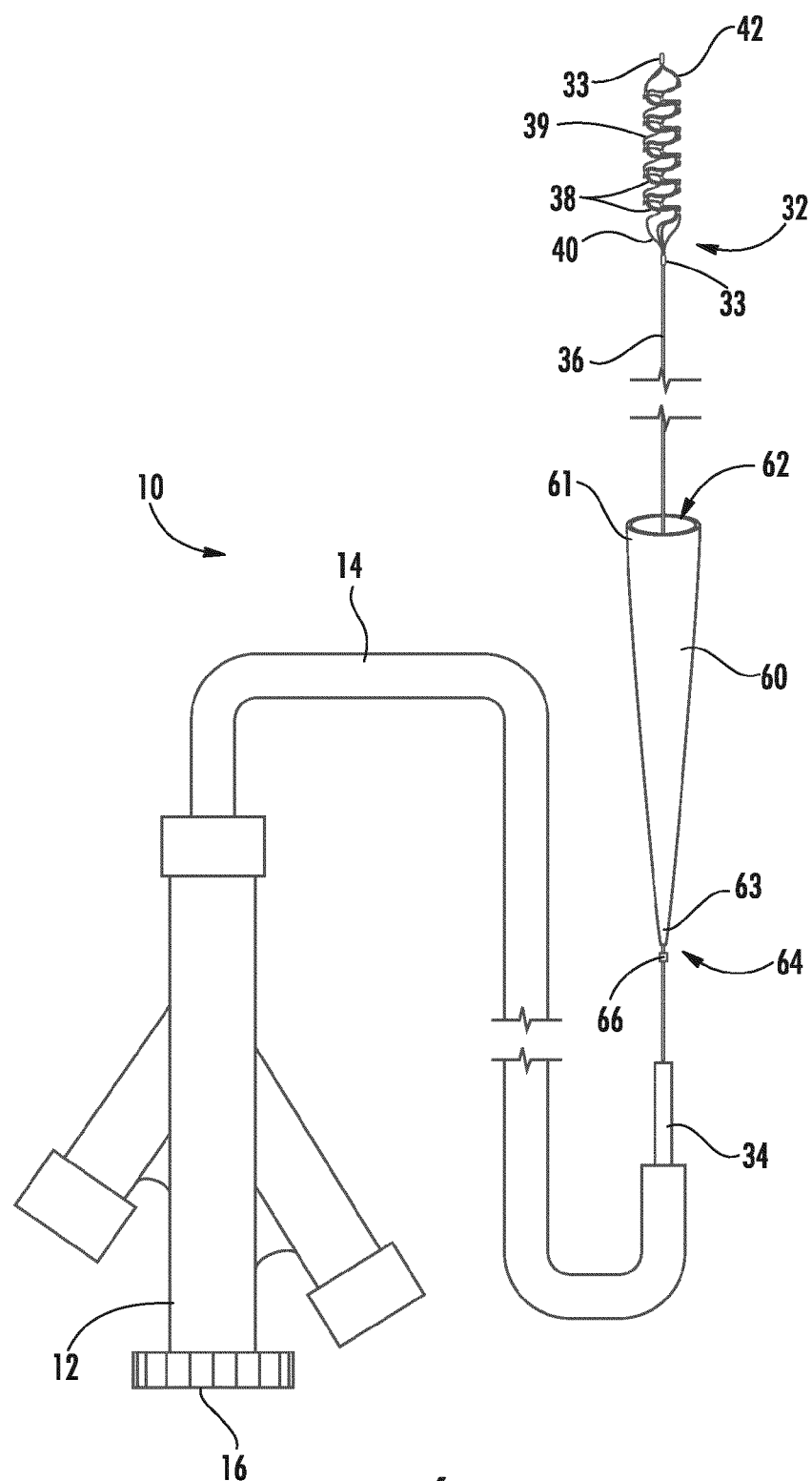
FIG. 6 is a side view of a catheter device, according to another exemplary embodiment.
Figure 7A:
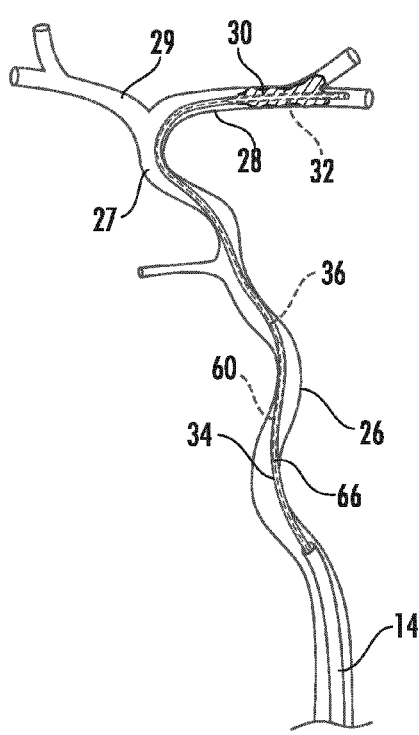
FIGS. 7A-7C depict the catheter device of FIG. 6 being used to remove a thrombus, according to an exemplary embodiment.
Figure 7B:
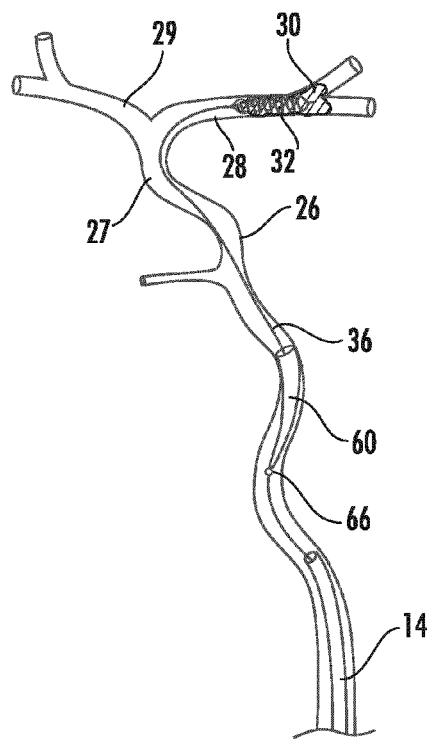
Figure 7C:
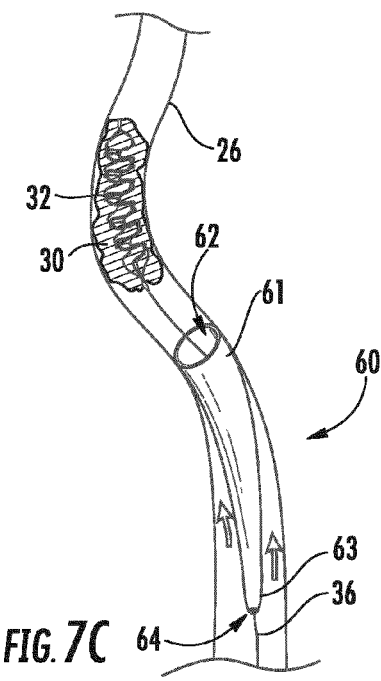
Figure 8:
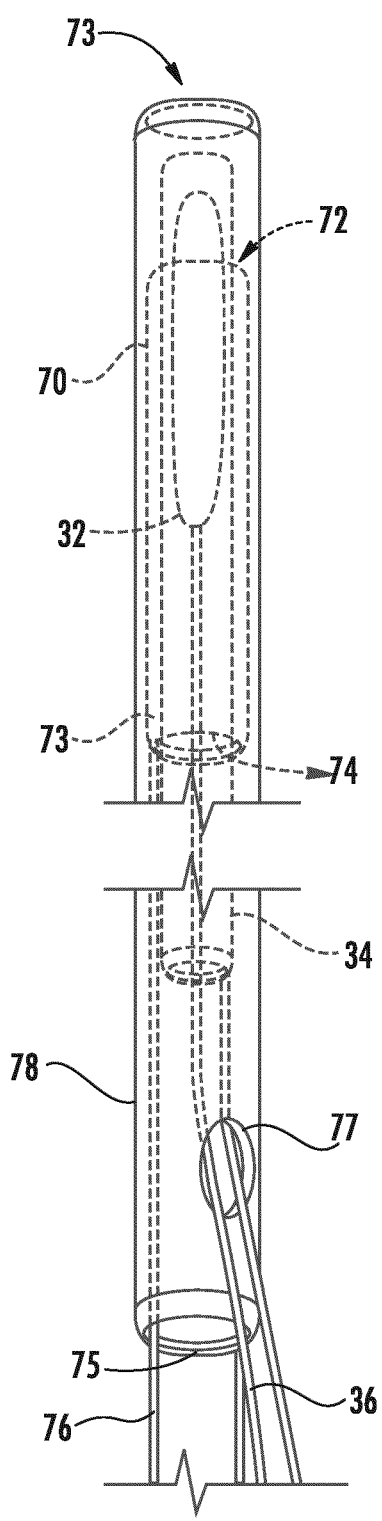
FIG. 8 is a perspective view of a portion of a catheter device, according to another exemplary embodiment.

Referring now to FIGS. 6-7C, in some embodiments, the catheter device 10 may further include a flexible sheath 60 (e.g., cover, shroud, sleeve, etc.). The sheath 60 is a tubular member that is configured to envelop or engulf the stent retriever 32 and the removed thrombus 30. The sheath 60 is formed from a flexible bio-compatible polymer or metal wire mesh. The sheath 60 is formed from a tight mesh to secure the thrombus and prevent fragments of the thrombus 30 from escaping as the thrombus 30 is being removed from the blood vessel. The sheath 60 forms a distal opening 62 through which the stent retriever 32 and the thrombus 30 may be retracted into the sheath 60 and a smaller proximal opening 64. In an expanded configuration, the distal opening 62 of the sheath 60 is large enough and the sheath 60 has a length that is large enough to receive the stent retriever 32 and the removed thrombus 30. In one embodiment, the sheath 60 has a distal opening 62 with a diameter of between 4 mm and 7 mm and a length of between 20 mm and 60 mm. The proximal opening 64 is large enough to allow the push wire 36 of the stent retriever 32 to pass freely through the sheath 60 without binding but does not allow the stent retriever 32 to pass through. A mechanism, shown as a stopper 66 provided at a point along the length of the push wire 36, limits the travel of the stent retriever 32 relative to the sheath 60. The stopper 66 has a diameter larger than the diameter of the proximal opening 64.

Referring to FIG. 7A, the sheath 60 is advanced through the patient's vascular system in a collapsed configuration within a catheter. For example, according to one embodiment, the sheath 60 is collapsed within the microcatheter 34 with the stent retriever 32. The microcatheter 34 is advanced along a microwire 44 to pass though the thrombus 30, as described above with respect to FIG. 4B. With the microcatheter 34 in place, the microwire 44 is retracted and the stent retriever 32 and the sheath 60, both in a collapsed configuration, are fed through the microcatheter 34 until the stent retriever 32 passes through the thrombus 30. The sheath 60 is advanced through the microcatheter 34 through the interaction between the stopper 66 and the proximal portion 63 of the sheath 60.

Referring to FIG. 7B, the stent retriever 32 is held stationary by fixing the push wire 36 at the base 12 of the catheter device 10. The microcatheter 34 is retracted to unsheathe the stent retriever 32 and the sheath 60. The stent retriever 32 expands to compress the thrombus 30 against the walls of the blood vessel. The sheath 60 is disposed in the patient's blood vessel at some point upstream from the stent retriever 32 and the thrombus 30. The sheath 60 may be provided at any distance from the thrombus 30, depending on the position of the stopper 66. In an exemplary embodiment, the stopper 66 is disposed along the push wire 36 between 3 cm and 12 cm from the stent retriever 32. In some embodiments, the positioning of the sheath 60 relative to the thrombus 30 is determined based on the size and shape of the blood vessel. The sheath 60 is expanded when outside the microcatheter 34. In some embodiments, the diameter of the distal portion 61 of the sheath 60 is equal to the inner diameter of the blood vessel (e.g., the internal carotid artery 26) so that the distal portion 61 of the sheath 60 occludes the blood vessel and temporarily prevents the flow of blood past the stent retriever 32 as the thrombus 30 is being retracted towards the sheath 60, minimizing the likelihood of fragmentation of the thrombus 30. In other embodiments, the sheath 60 may not occlude the blood vessel and the blood vessel may be otherwise occluded, such as via the inflation of a balloon upstream from the sheath 60.

Referring to FIG. 7C, the push wire 36 is released and the stent retriever 32 is withdrawn, removing the thrombus 30 in the process. The sheath 60 remains stationary as the stent retriever 32 and the removed thrombus 30 are retracted. The stent retriever 32 and the removed thrombus 30 are moved into the sheath 60, which is withdrawn from the vascular system along with the stent retriever 32 and the removed thrombus 30. The sheath 60 protects the stent retriever 32 and the removed thrombus 30 during the withdrawal process.

Figure 9:
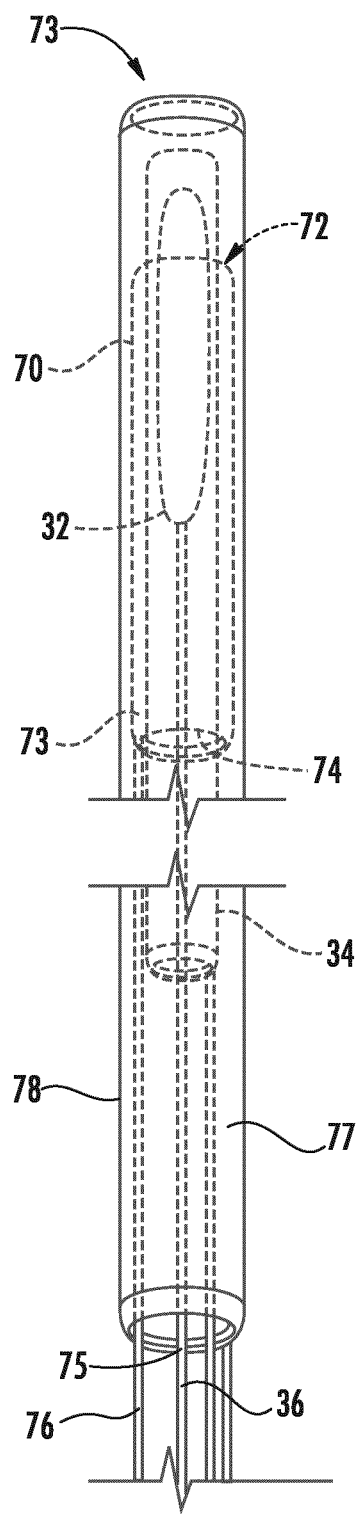
FIG. 9 is a perspective view of a portion of a catheter device, according to another exemplary embodiment.

Referring now to FIGS. 8-10C, in some embodiments, the catheter device 10 may include a flexible sheath 70 (e.g., cover, shroud, sleeve, etc.) that may be added to an existing stent retriever system. The sheath 70 is similar to sheath 60 and is a tubular member that is configured to envelop or engulf the stent retriever 32 and the removed thrombus 30. The sheath 70 defines a distal opening 72 and a proximal opening 74. A push wire 76 is coupled to the proximal portion 74 of the sheath 70. According to an exemplary embodiment, the push wire 76 has a diameter of between 0.07" and 0.14". According to another exemplary embodiment, the push wire 76 has a diameter of between 0.07" and 0.10". The microcatheter 34 passes through the proximal opening 74 and through the distal opening 72. In an expanded configuration, the distal opening 72 of the sheath 70 is large enough and the sheath 70 has a length that is large enough to receive the stent retriever 32 and the removed thrombus 30, similar to the sheath 60, as shown in FIG. 6. The proximal opening 74 is large enough to allow the microcatheter 34 to pass freely through the sheath 70 without binding. The sheath 70 and the stent retriever 32, which is compressed within the microcatheter 34, are housed within an outer microcatheter 78. The outer microcatheter 78 defines a distal opening 73, a proximal opening 75 through which the push wire 76 passes, and, in the embodiment of FIG. 8, a side opening 77 through which the microcatheter 34 passes. The embodiment shown in FIG. 9 is similar to that of FIG. 8, except that the outer microcatheter 78 does not include a side opening 77 and microcatheter 34 passes through the proximal opening 75 of the outer microcatheter 78.

The sheath 70 may be used with an existing stent retriever system by first inserting the sheath 70 into the outer microcatheter 78 through the proximal opening 75. The microcatheter associated with the existing stent retriever system may be inserted through the side opening 77, into the interior of the outer microcatheter 78, through the proximal opening 74 and the distal opening 72 of the sheath 70, and through the distal opening 73 of the outer microcatheter 78. In another embodiment, the sheath 70 may be inserted into the outer microcatheter 78 through the side opening 77. The microcatheter associated with the existing stent retriever system may be inserted through the proximal opening 75, into the interior of the outer microcatheter 78, through the proximal opening 74 and the distal opening 72 of the sheath 70, and through the distal opening 73 of the outer microcatheter 78. The outer microcatheter 78 may then be inserted into the body via the RHV 16 of the base 12 and the guide catheter 14.

Figure 10A:
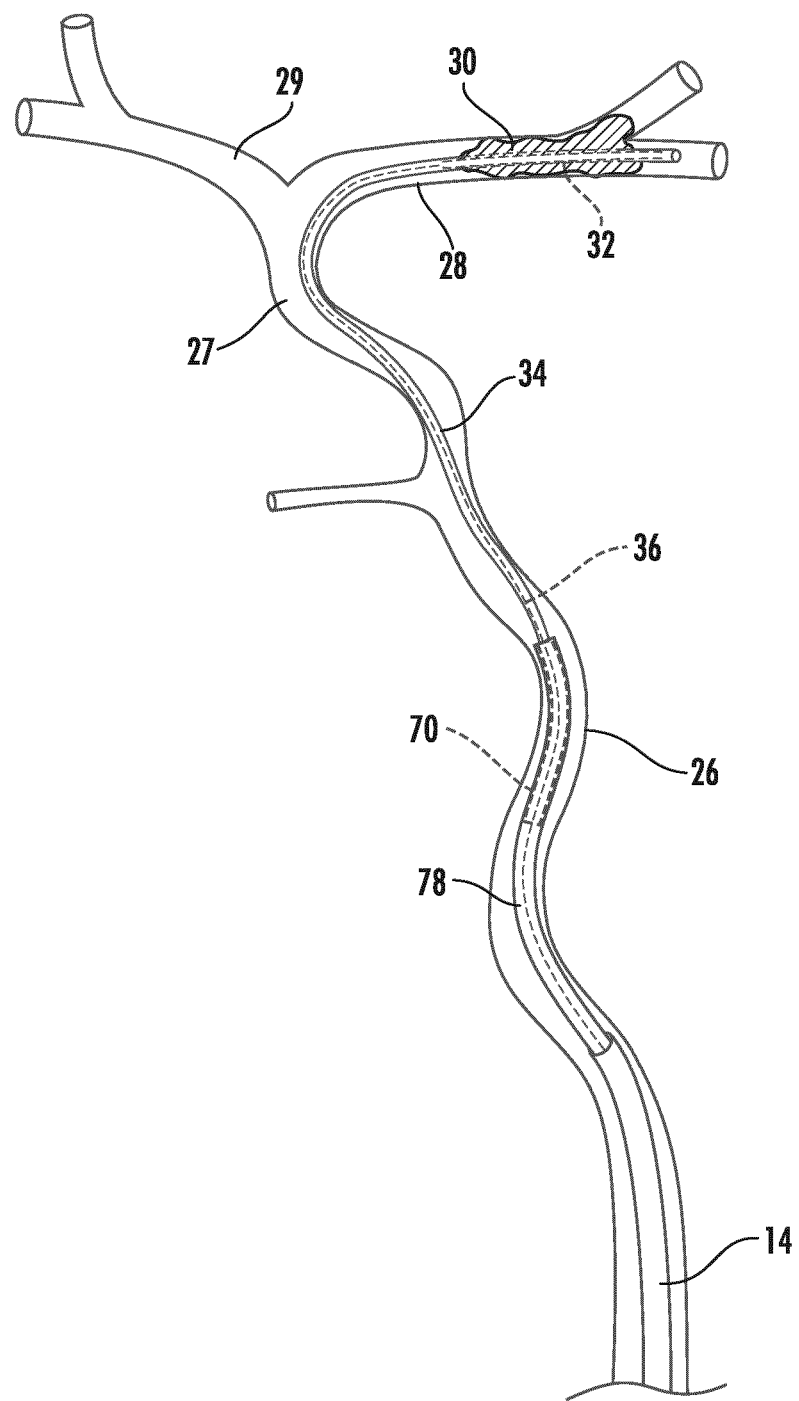
FIGS. 10A-10C depict the catheter device of FIG. 8 or FIG. 9 being used to remove a thrombus, according to an exemplary embodiment.

Referring to FIG. 10A, the guide catheter is advanced through the patient's vascular system to a position below (e.g., upstream) from the thrombus 30. The guide catheter 14 is then retracted to expose the outer microcatheter 78. The outer microcatheter 78 is fixed in place and the sheath is fixed in place via the push wire 76. The microcatheter 34 is advanced to pass though the thrombus 30 over a microwire. With the microcatheter 34 in place, the microwire is retracted and the stent retriever 32, in a collapsed configuration, is fed through the microcatheter 34 until it passes through the thrombus 30 to a point distal to the thrombus 30. In some embodiments, the stent retriever 32 is positioned with the aid of the radiopaque markers 33.

Figure 10B:
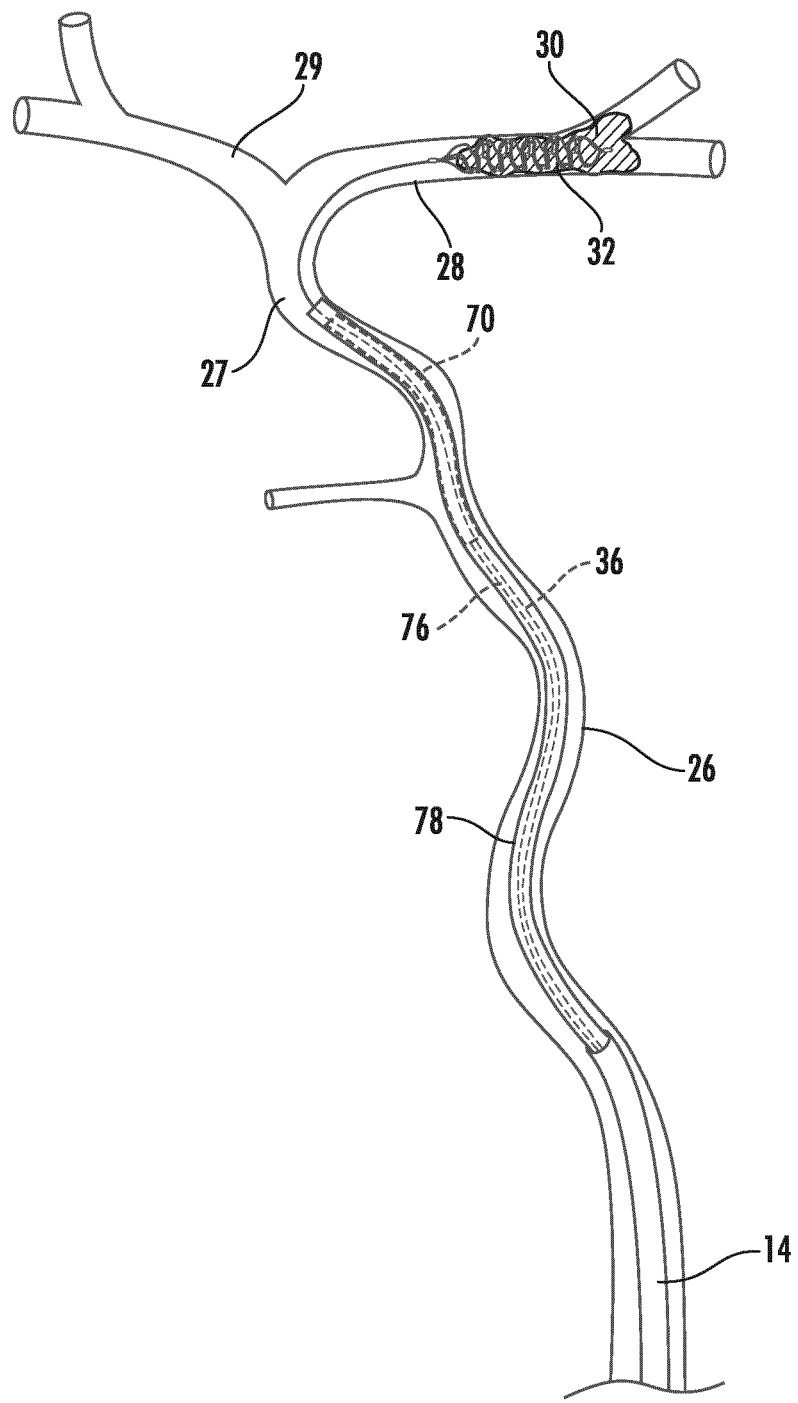

Referring to FIG. 10B, the stent retriever 32 is held stationary by fixing the push wire 36 at the base 12 of the catheter device 10. The microcatheter 34 is retracted to unsheathe the stent retriever 32. The stent retriever 32 expands to compress the thrombus 30 against the walls of the blood vessel. The sheath 70 is positioned independently of the stent retriever 32. The sheath 70 and/or the outer microcatheter 78 can be advanced to any desired location relative to the thrombus 30. For example, as illustrated in FIG. 10B, the outer microcatheter 78 may be advanced to a point in the blood vessel in close proximity to the thrombus 30, minimizing the distance traveled by the stent retriever 32 and the removed thrombus 30 before being received by the sheath 70. However, in other embodiments, the outer microcatheter 78 may be advanced to a point further upstream from the thrombus 30. In some embodiments, the positioning of the outer microcatheter 78 and the sheath 70 relative to the thrombus 30 is determined based on the size and shape of the blood vessel.

Figure 10C:
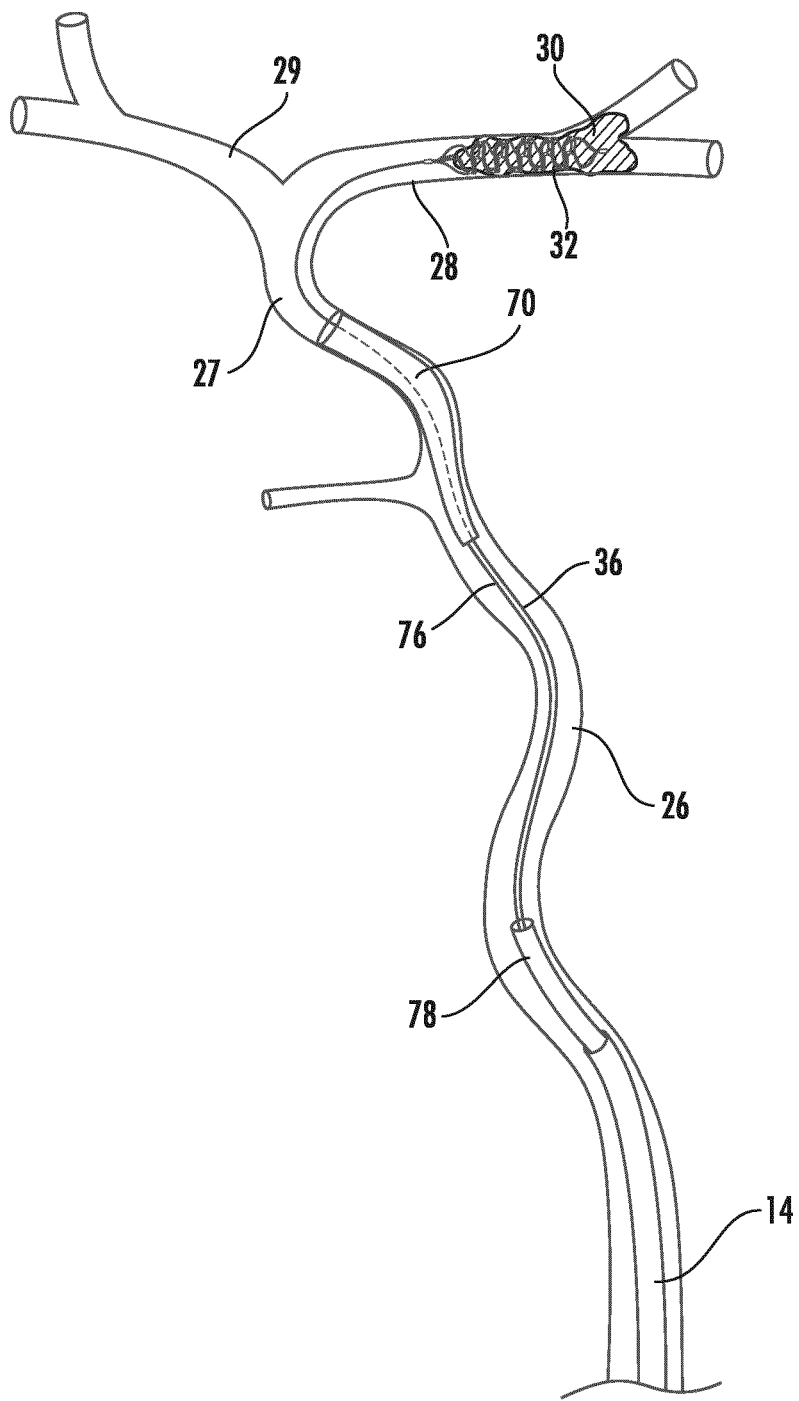

Referring to FIG. 10C, the sheath 70 is then deployed by fixing the push wire 76 and retracting the outer microcatheter 78. The sheath 70 is expanded when outside the outer microcatheter 78, as described above with respect to the sheath 60. In some embodiments, the sheath 70 may be completely deployed from the outer microcatheter 78, as illustrated in FIG. 10C. In other embodiments, the sheath 70 may only be partially deployed from the outer microcatheter 78 such that it forms a funnel structure for receiving the stent retriever 32 and the removed thrombus 30 in the outer microcatheter 78. Once the sheath 70 is deployed, the push wire 36 is released and the stent retriever 32 is withdrawn, removing the thrombus 30 in the process. The sheath 70 remains stationary as the stent retriever 32 and the removed thrombus 30 are retracted. The stent retriever 32 and the removed thrombus 30 are moved into the sheath 70, which is withdrawn from the vascular system along with the stent retriever 32 and the removed thrombus 30. The sheath 70 protects the stent retriever 32 and the removed thrombus 30 during the withdrawal process. According to some embodiments, the sheath 70 and the stent retriever 32 may be loaded separately over the push wire 76. According to some embodiments, the sheath 70 and the stent retriever 32 may be combined as one piece covered retriever. According to some embodiments, the sheath 70 and the stent retriever 32 may be retrieve simultaneously.

While the stent retriever in FIGS. 5A-7C is shown as the stent retriever 32, the sheaths 60, 70, or 80 may be configured for use with any existing stent retriever designs. For example, the sheaths 60, 70, and 80 may be configured for use with the Solitaire™ revascularization device, marketed by Medtronic; the Mindframe device, marketed by Medtronic; the Trevo® device, marketed by Stryker; the Embotrap revascularization device, marketed by Neuravi; or any other similar devices.

Figure 11:
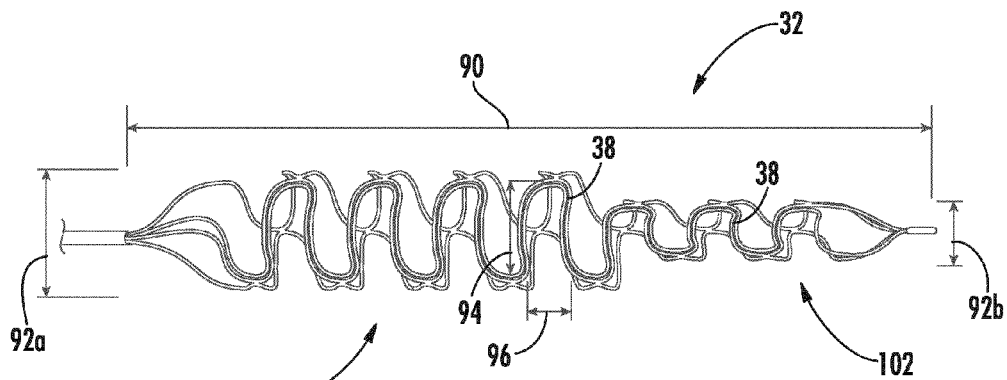
FIG. 11 is a perspective view of a stent retriever, according to another exemplary embodiment.
Figure 12:
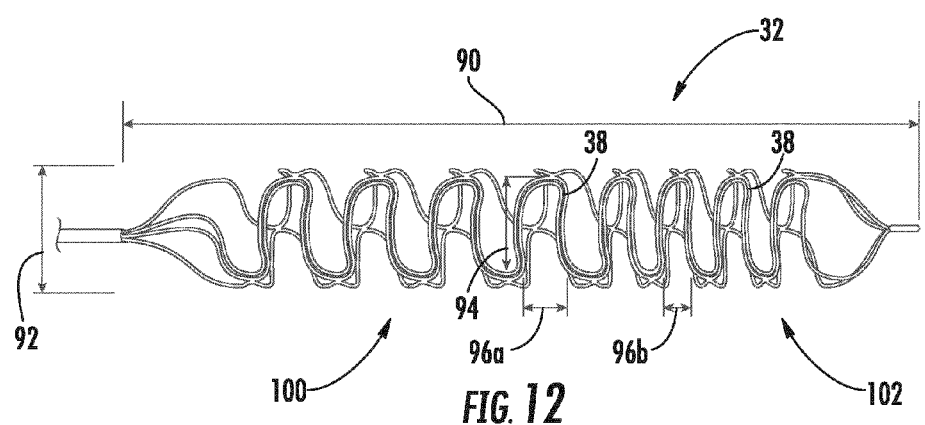
FIG. 12 is a perspective view of a stent retriever, according to another exemplary embodiment.
Figure 13:
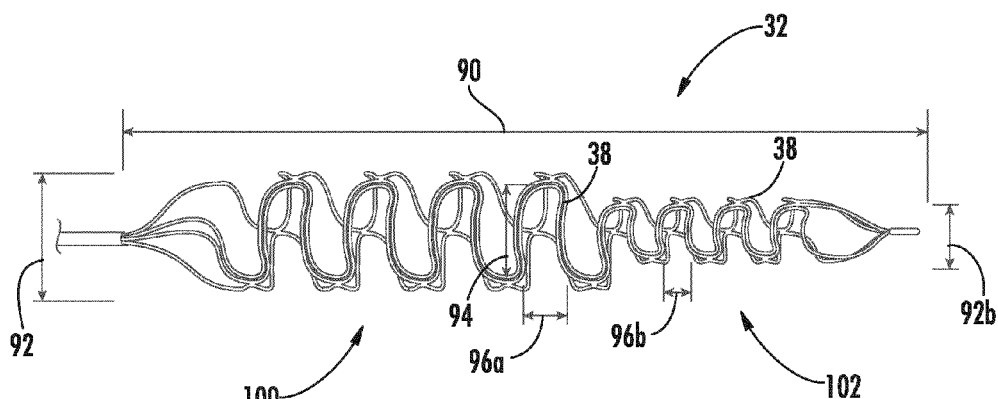
FIG. 13 is a perspective view of a stent retriever, according to another exemplary embodiment.

Referring now to FIGS. 11-13, the stent retriever 32 is shown according to other exemplary embodiments. The stent retriever 32 has a length 90 and a diameter 92. The protrusions 38 are shown to have a length 94, and a width 96. Referring back to FIGS. 3A-C in one embodiment, the width 96 of the protrusions 38 and the diameter 92 may be constant. As shown in FIG. 3B, the interlocking protrusions 38 may have a length 94 such that they comprise approximately ⅓ of the total circumference of the stent retriever. In other embodiments, the length 94 of the protrusions may be greater, such that they comprise a greater portion of the total circumference of the stent retriever 32 or may be lesser, such that they comprise a lesser portion of the total circumference of the stent retriever 32.

In another embodiment, the diameter 92 of the stent retriever 32 and the density (e.g., wire density, mesh density, etc.) of the stent retriever 32 may vary along the length of the stent retriever 32. The diameter 92 of a first portion of the stent retriever 32 may be diameter and the diameter 92 of a second portion of the stent retriever 32 may have a different diameter. For example, as shown in FIG. 11, a proximal portion 100 of the stent retriever 32 may have a first diameter 92*a* and a distal portion 102 of the stent retriever 32 may have a second diameter 92*b* that is less than the first diameter 96*a*. In this way the mesh density of the distal portion 102 may be greater than the density of the proximal portion 100. In some embodiments, the diameter 92 is decreased gradually along the length 90, so that at the distal end of the stent retriever 32, the diameter 92 is smaller than the proximal end of the stent retriever 32. In some embodiments, the diameter 92 is increased gradually along the length 90, so that at the distal end of the stent retriever 32 the diameter 92 is larger than then the proximal end of the stent retriever 32.

In another embodiment, the width 96 of the protrusions 38 and the density (e.g., wire density, mesh density, etc.) of the stent retriever 32 may vary along the length of the stent retriever 32. The protrusions 38 of a first portion of the stent retriever 32 may have a width and the protrusions 38 of a second portion of the stent retriever 32 may have a different width. For example, as shown in FIG. 12, the protrusions 38 of the proximal portion 100 of the stent retriever 32 may have a first width 96*a* and the protrusions 38 of the distal portion 102 of the stent retriever 32 may have a second width 96*b* that is less than the first width 96*a*. In this way the mesh density of the distal portion 102 may be greater than the density of the proximal portion 100.

In another embodiment, both the diameter 92 of the stent retriever 32 and width 96 of the protrusions 38 may vary along the length of the stent retriever 32. For example, as shown in FIG. 13, the diameter 92*a* of the proximal portion 100 of the stent retriever 32 may be greater than the diameter 92*b* of the distal portion 102 and the width 96*a* of the protrusions 38 of the proximal portion 100 may be greater than the width 96*b* of the protrusions 38 of the distal portion 102.

Figure 14:
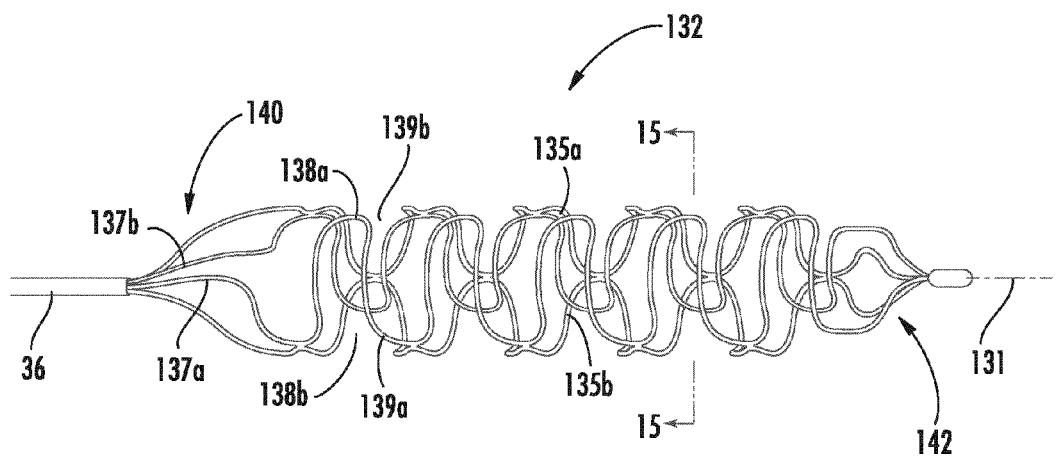
FIG. 14 is a perspective view of a stent retriever, according to another exemplary embodiment.
Figure 15:
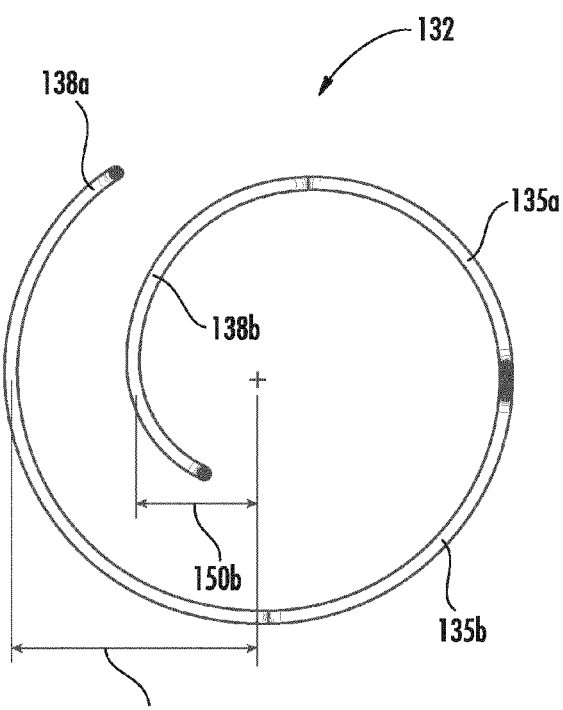
FIG. 15 is a cross-section view schematic illustration of the stent retriever of FIG. 14, taken along line 15-15.

Referring now to FIGS. 14-15, a stent retriever 132 is shown according to another exemplary embodiment with overlapping protrusions 138. FIG. 14 depicts a side view of stent retriever 132 and FIG. 15 depicts an end view of stent retriever 132, showing overlapping protrusions 138*a* and 138b when the stent sheet is formed into a cylindrical body. Similar to the stent retriever 32, the stent retriever 132 is formed from a suitable biocompatible metal or alloy (e.g., platinum, stainless steel, nickel-titanium alloy, etc.) or a suitable biocompatible polymer. The stent retriever 132 may be self-expandable or may be expanded with another device, such as an inflatable balloon. All or part of the stent retriever 132 may be coated or covered with a radiopaque material, such as platinum to allow for visualization of the stent retriever 132. The stent retriever 132 includes a proximal 140 end and a distal end 142.

The stent retriever 132 is an open, generally cylindrical body that includes a multitude of protrusions 138a and 138b (e.g., fingers, projections, arms, etc.). According to one exemplary embodiment, a row of first protrusions 138a are formed from a first undulating wire member 137a. The protrusions 138a are formed as U-shaped members that are oriented laterally (e.g., generally perpendicular to a longitudinal axis 131 of the stent retriever 132). A row of second protrusions 138b are formed from a second undulating wire member 137b. The protrusions 138b are formed as U-shaped members that are oriented laterally (e.g., generally perpendicular to the longitudinal axis 131 of the stent retriever 132).

The wire members 137a and 137b are coupled to each other with connecting members 135. According to an exemplary embodiment, the connecting members 135 are undulating (e.g., sinusoidal) wire members that are coupled to the portions of the wire members 137a and 137b forming the recesses 139a and 139b. In other embodiments, the connecting members may be otherwise configured. For example, in another embodiment, the wire members 137a and 137b may be coupled to each other with a multitude of linear connecting members that extend laterally around the outer circumference of the stent retriever 30 between the wire members 137a and 137b. In some embodiments, the connecting members 135 are fixed to the wire members 137a and 137b. In some embodiments, the connecting members 135 and the wire members 137a and 137b may be interwoven (e.g., twisted together) such that the wire members slide relative to each other as the stent retriever 132 expands or compresses in diameter.

The protrusions 138a and 138b are disposed in an overlapping arrangement such that the protrusions 138a overlap (e.g., pass over, pass under, etc.) the protrusions 138b. The protrusions 138a are formed with a first radius 150a and the protrusions 138b are formed with a second radius 150b that is less than the first radius 150a. According to an exemplary embodiment, the second radius 150b is between 25% and 100% of the first radius 150a. According to a preferred embodiment, the second radius 150b is approximately 50% of the first radius 150a. By providing the protrusions 138a and 138b at different radii, the protrusions 138a and 138b can interact with the thrombus 30 in different ways. For example, in one embodiment, the protrusions 138b have a radius that is less than the radius of the thrombus 30. Therefore, when the stent retriever 132 is advanced into the thrombus 30 and expanded, the protrusions 138b anchor the thrombus 30 to the stent retriever 132. Meanwhile, the protrusions 138a surround the thrombus 30 and prevent the escape of the thrombus 30 as the stent retriever 132 is retracted.

In some embodiments, the protrusions 138a and 138b may be formed with different densities. In one embodiment, the protrusions 138a are formed with a relatively dense mesh to reduce the likelihood that any portion of the thrombus escapes as the stent retriever 132 is retracted while the protrusions 138b are formed with a relatively loose mesh to reduce unnecessary fragmentation of the thrombus 30.

Figure 16:
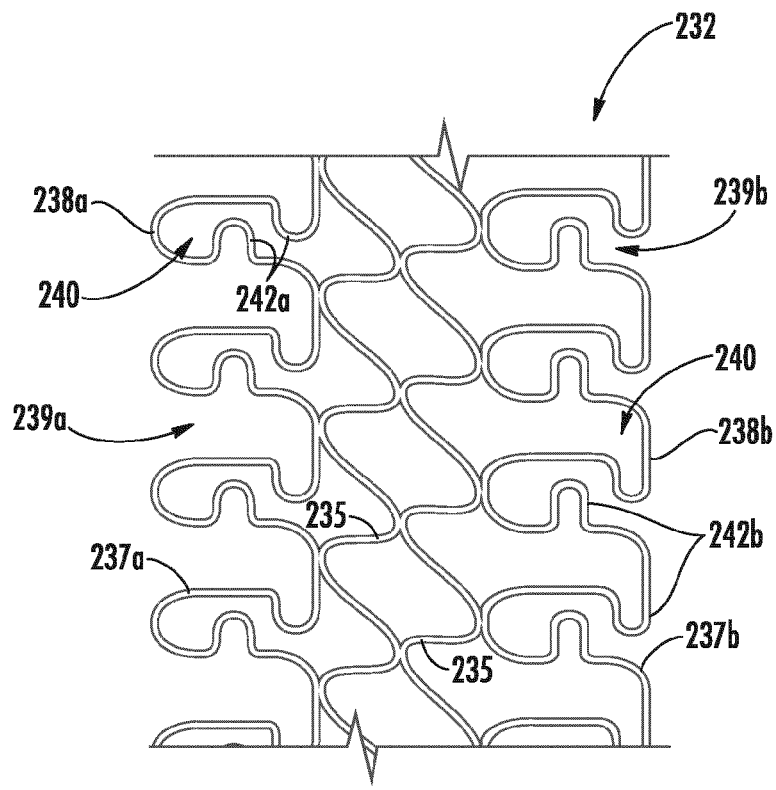
FIG. 16 is a side view of a stent retriever according to an exemplary embodiment, shown opened from a cylindrical form.

Referring now to FIG. 16, an illustration of an opened, substantially flat view of a mesh sheet of another stent retriever 232 is shown. The stent retriever 232 is configured similar to the stent retriever 32 described above and includes a first undulating wire member 237a and a second wire member 237b. The wire members 237a and 237b are coupled to each other with connecting members 235. The first wire member 237a forms a row of first protrusions 238a and recesses 239a. The second wire member 237b forms a row of second protrusions 238b and recesses 239b. The protrusions 238a and 238b are disposed in an interlocking (e.g., interdigitated) arrangement such that the protrusions 238a are received in the recesses 239b and the protrusions 238b are received in the recesses 239a.

According to an exemplary embodiment, one or more of the protrusions 238a and 238b are formed to include sub-protrusions 242a and 242b, increasing the mesh density of the stent retriever 232. Increasing the mesh density of the stent retriever 232 reduces the likelihood that a portion of the thrombus 30 will escape the stent retriever 232. The sub-protrusions 242a extend into the U-shaped openings 240, decreasing the area of the openings 240. The sub-protrusions 242b extend out from the U-shaped openings 240. Sub-protrusions 242b are configured to be received by sub-protrusions 242a when the stent retrieve 232 is formed into a cylindrical body. In the embodiment of FIG. 16, the sub-protrusions 242a and 242b are formed as U-shaped members. In other embodiments, the sub-protrusions may be otherwise formed, such as in a saw-tooth pattern. Similar to the embodiment of FIGS. 3C-3D, the protrusions 238 of stent retriever 232 may also be formed with a curve or at an angle, such that the protrusions extend into the bore of the cylindrical stent retriever body.

Figure 17:
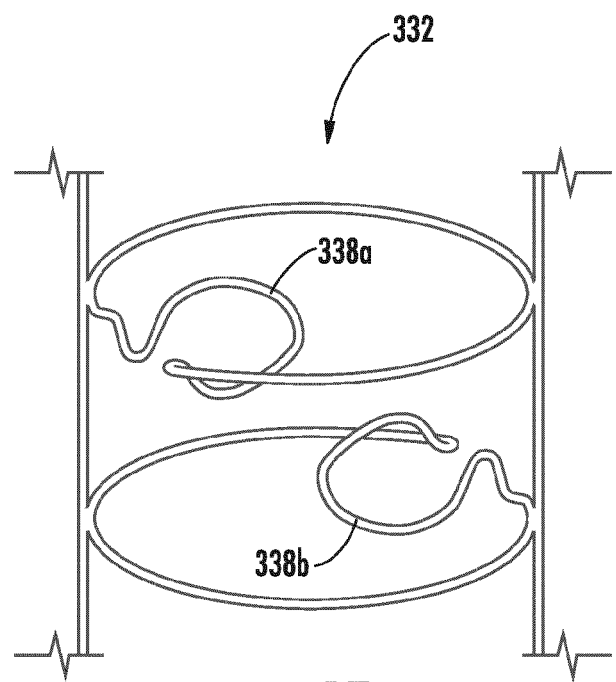
FIG. 17 is a perspective view of a stent retriever according to one or more exemplary embodiments.

Referring now to FIG. 17, a perspective view of a stent retriever 332 is shown according to one or more embodiments. The stent retriever 332 includes multiple protrusions 338a and 338b. The protrusions 338a and 338b extend inward from the outer periphery of the stent retriever 332. According to some embodiments, the opening of the protrusions 338a and 338b are arranged to face different directions, so that the protrusion 338a and protrusion 338b do not meet at the center of the circle. For example, the opening of the protrusion 338a may face a direction with a desired angle to the direction of the protrusion 338b. According to some embodiments, the protrusion 338a and the protrusion 338b are arranged to maximize the contact area between the stent retriever 332 and thrombus in order to reduce the likelihood that the thrombus will escape as the stent retriever 332 is retracted.

Figure 18:
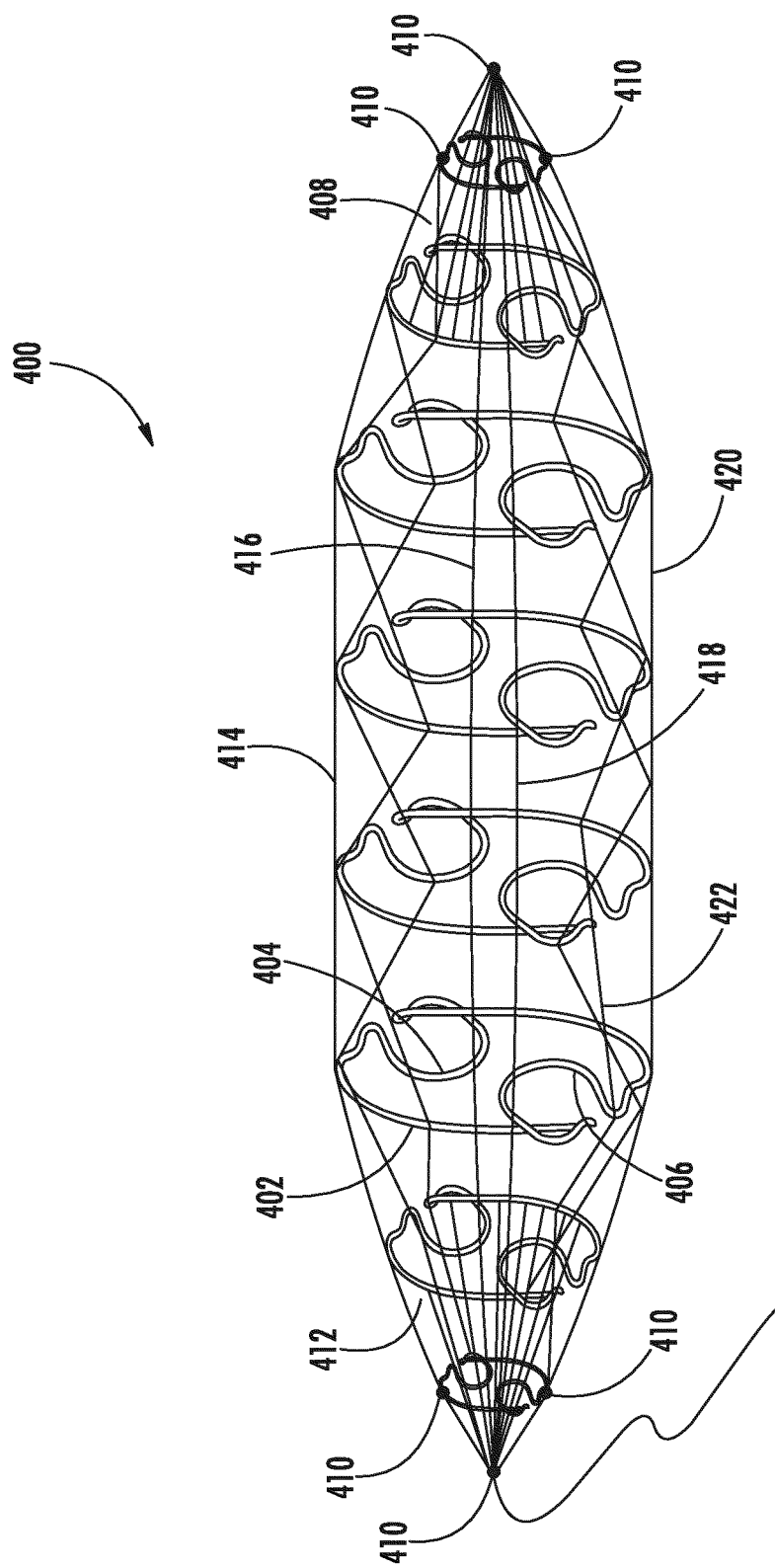
FIG. 18 is a perspective view of a stent retriever according to one or more exemplary embodiments.

Referring to FIG. 18, a perspective view of a stent retriever 400 is shown according to one or more embodiments. The retriever 400 includes multiple circular elements 402. According to some embodiments, the number of the circular elements 402 of the retrievers 400 may be determined according to the size of the thrombus. According to some embodiments, the circular elements 402 may have different sizes. For example, the circular element in the middle of the retriever 400 has larger size than the circular element in a distal end and circular element in a proximal end of the retriever 400. According to some embodiments, the size of the circular elements 402 may be gradually decreased from middle portion to the end portions.

The circular element 402 includes a protrusion 404 and protrusion 406. According to some embodiments, the protrusions 404 and 406 are formed as U-shaped members.

According to some embodiments, the openings of the protrusions 404 and 406 are arranged to face different directions to provide larger contact area between the stent retriever 400 and thrombus in order to reduce the likelihood that the thrombus will escape as the retriever 400 is retracted. For example, if viewing the circular element 402 as a clock, the protrusion 404 faces 1 o'clock direction, and the protrusion 406 faces 7 o'clock direction.

According to some embodiments, the circular elements 402 are connected with each other by four straight wires 414, 416, 418, and 420. According to some embodiments, the four straight wires divided the retriever 400 into four equal zones. According to some embodiments, within each zone, a zigzag wire 422 is connected to each circular element 402 to hold the circular element in place. According to some embodiments, at the distal and proximal end of the retriever, multiple straight wires are connected to one or two circular elements to form a mesh zone in order to capture any fragments of the thrombus.

The retriever 400 further includes three opaque markers 410 at each end of the retriever 400. The opaque markers 410 may be used to aid in the positioning of the stent retriever 400 relative to the thrombus according to some embodiments.

The construction and arrangement of the elements of the catheters for engulfing thrombi as shown in the various exemplary embodiments is illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited herein. For example, elements shown as integrally formed may be constructed of multiple parts or elements, the position of elements may be reversed or otherwise varied, and the nature or number of discrete elements or positions may be altered or varied. It should be noted that the elements and/or assemblies of the system may be constructed from any of a wide variety of materials that provide sufficient strength, durability, or biocompatibility. Other substitutions, modifications, changes and omissions may be made in the design, operating conditions and arrangement of the preferred and other exemplary embodiments and medical procedures without departing from the scope of the present invention.

What is claimed is:

1. A system for removing a thrombus from a blood vessel, the system comprising:
    a stent retriever, the stent retriever comprising:
        a body portion formed by a mesh sheet formed into a substantially cylindrical shape;
        wherein the mesh sheet comprises a pair of undulating wire members coupled to a connecting member, each of the pair of wire members comprising a plurality of protrusions, and a plurality of recesses defined between the plurality of protrusions;
        wherein the plurality of protrusions on a first side of the mesh sheet are offset from the plurality of protrusions on a second side of the mesh sheet such that when the mesh sheet is formed into the substantially cylindrical shape by bringing the first and second side of the mesh sheet together, the wire members are disposed in an interlocking arrangement such that the plurality of recesses on the first side of the mesh sheet receive at least portions of the plurality of protrusions on the second side of the mesh sheet; and
        wherein the plurality of protrusions on the first and second side of the mesh sheet are curved upward from the connecting member of the mesh sheet such that when the mesh sheet is formed into the substantially cylindrical shape, the protrusions alternatingly extend into a bore of the substantially cylindrical body portion;
    a sheath comprising a tubular body and defining a distal opening and a proximal opening;
    a catheter configured to receive the stent retriever in a collapsed configuration and the sheath in a collapsed configuration, wherein the stent retriever is and the sheath are movable relative to the catheter; and
    a wire coupled to the stent retriever for positioning the stent retriever, the wire extending through the proximal opening and the distal opening of the sheath;
    wherein the stent retriever is moveable relative to the sheath; and
    wherein the distal opening of the sheath is sized to allow the stent retriever to be withdrawn into the sheath without substantially compressing the stent retriever.

2. The system of claim 1, wherein the proximal opening of the sheath is sized to prevent the passage of the withdrawn stent retriever.

3. The system of claim 1, further comprising a second wire coupled to the sheath.

4. The system of claim 3, wherein the catheter is a first catheter and the sheath is provided in a collapsed configuration within a second catheter, and wherein the first catheter passes through the distal opening and the proximal opening of the sheath.

5. The system of claim 4, wherein the first catheter passes through the distal opening and the proximal opening of the second catheter.

6. A system for removing a thrombus from a blood vessel, the system comprising:
    a stent retriever;
    a catheter configured to receive the stent retriever in a collapsed configuration, wherein the stent retriever is movable relative to the catheter;
    a sheath comprising a tubular body and defining a distal opening and a proximal opening;
    a wire coupled to the stent retriever for positioning the stent retriever, the wire extending through the proximal opening and the distal opening of the sheath;
    wherein the stent retriever is moveable relative to the sheath; and
    wherein the distal opening of the sheath is sized to allow the stent retriever to be withdrawn into the sheath without substantially compressing the stent retriever;
    a stopper fixed to the wire; and
    wherein the diameter of the stopper is larger than the diameter of the proximal opening of the sheath to limit the travel of the stent retriever relative to the sheath.

7. The system of claim 6, wherein the sheath is provided in a collapsed configuration within the catheter and is deployed from the catheter via the interaction of the stopper and the sheath by retracting the catheter from the stent retriever.

8. The system of claim 6, wherein the stent retriever comprises:
    a body portion formed by a mesh sheet formed into a substantially cylindrical shape;
    wherein the mesh sheet comprises a pair of undulating wire members coupled to a connecting member, each of the pair of wire members comprising a plurality of protrusions, and a plurality of recesses defined between the plurality of protrusions;

wherein the plurality of protrusions on a first side of the mesh sheet are offset from the plurality of protrusions on a second side of the mesh sheet such that when the mesh sheet is formed into the substantially cylindrical shape by bringing the first and second side of the mesh sheet together, the wire members are disposed in an interlocking arrangement such that the plurality of recesses on the first side of the mesh sheet receive at least portions of the plurality of protrusions on the second side of the mesh sheet; and wherein the plurality of protrusions on the first and second side of the mesh sheet are curved upward from the connecting member of the mesh sheet such that when the mesh sheet is formed into the substantially cylindrical shape, the protrusions alternatingly extend into a bore of the substantially cylindrical body portion.

9. A system for removing a thrombus from a blood vessel, the system comprising:
a stent retriever;
a first catheter configured to receive the stent retriever in a collapsed configuration, wherein the stent retriever is movable relative to the first catheter;
a sheath comprising a tubular body and defining a distal opening and a proximal opening;
a wire coupled to the stent retriever for positioning the stent retriever, the wire extending through the proximal opening and the distal opening of the sheath;
a second wire coupled to the sheath;
wherein the stent retriever is moveable relative to the sheath; and
wherein the distal opening of the sheath is sized to allow the stent retriever to be withdrawn into the sheath without substantially compressing the stent retriever;
wherein the sheath is provided in a collapsed configuration within a second catheter having a distal opening and a proximal opening, and wherein the first catheter passes through the distal opening and the proximal opening of the sheath; and
a side opening defined in a side wall of the second catheter between the distal opening and the proximal opening.

10. The system of claim 9, wherein the first catheter passes through the distal opening and the side opening of the second catheter.

11. The system of claim 10, wherein the movement of the stent retriever and the movement of the sheath are independent of each other.

12. A system for removing a thrombus from a blood vessel, the catheter device comprising:
a stent retriever, the stent retriever comprising:
a body portion formed by a mesh sheet formed into a substantially cylindrical shape;
wherein the mesh sheet comprises a pair of undulating wire members coupled to a connecting member, each of the pair of wire members comprising a plurality of protrusions, and a plurality of recesses defined between the plurality of protrusions;
wherein the plurality of protrusions on a first side of the mesh sheet are offset from the plurality of protrusions on a second side of the mesh sheet such that when the mesh sheet is formed into the substantially cylindrical shape by bringing the first and second side of the mesh sheet together, the wire members are disposed in an interlocking arrangement such that the plurality of recesses on the first side of the mesh sheet receive at least portions of the plurality of protrusions on the second side of the mesh sheet; and
wherein the plurality of protrusions on the first and second side of the mesh sheet are curved upward from the connecting member of the mesh sheet such that when the mesh sheet is formed into the substantially cylindrical shape, the protrusions alternatingly extend into a bore of the substantially cylindrical body portion;
a first catheter, the first catheter configured to receive the stent retriever in a collapsed configuration, wherein the stent retriever is movable relative to the first catheter; and
a guide catheter configured to receive the first catheter, the guide catheter comprising an expandable distal portion;
wherein the diameter of the expandable distal portion is variable between a minimum diameter in which the expandable distal portion comprises a generally cylindrical shape and a maximum diameter in which the expandable distal portion comprises a generally non-cylindrical shape;
wherein the stent retriever is moveable relative to the guide catheter;
wherein, when the distal portion is expanded to the maximum diameter, the distal portion defines an opening that is sized to allow the stent retriever to be withdrawn into the guide catheter without substantially compressing the stent retriever; and
wherein the guide catheter comprises one or more mechanisms to expand and contract the expandable distal portion, wherein the one or more mechanisms comprises at least one of a torque mechanism, a string mechanism, or a combination thereof.

13. The system of claim 12, further comprising one or more mechanisms to expand and contract the expandable distal portion.

14. The system of claim 13, wherein the one or more mechanisms comprise at least one of a torque mechanism, a string mechanism, a spring mechanism, or a combination thereof.

15. The system of claim 12, wherein the expandable distal portion, when expanded to the maximum diameter, occludes a blood vessel in which it is disposed.

16. A stent retriever for removing a thrombus from a blood vessel, the stent retriever comprising:
a body portion formed by a mesh sheet formed into a substantially cylindrical shape;
wherein the mesh sheet comprises a pair of undulating wire members coupled to a connecting member, each of the pair of wire members comprising a plurality of protrusions, and a plurality of recesses defined between the plurality of protrusions;
wherein the stent retriever is expandable from a compressed configuration to an expanded configuration;
wherein the plurality of protrusions on a first side of the mesh sheet are offset from the plurality of protrusions on a second side of the mesh sheet such that when the mesh sheet is formed into the substantially cylindrical shape by bringing the first and second side of the mesh sheet together, the wire members are disposed in an interlocking arrangement such that the plurality of recesses on the first side of the mesh sheet receive at least portions of the plurality of protrusions on the second side of the mesh sheet; and
wherein the plurality of protrusions on the first and second side of the mesh sheet are curved upward from the connecting member of the mesh sheet such that when the mesh sheet is formed into the substantially cylindrical shape, the protrusions alternatingly extend into a bore of the substantially cylindrical body portion.

17. The stent retriever of claim 16, further comprising a proximal portion having a first outer diameter and a distal portion having a second outer diameter;

wherein the first outer diameter is greater than the second outer diameter.

18. The stent retriever of claim 17, wherein the stent retriever has a gradually decreasing diameter from the first outer diameter to the second outer diameter.

19. The stent retriever of claim 16, further comprising a proximal portion having a first mesh density and a distal portion having a second mesh density;

wherein the first mesh density is less than the second mesh density.

20. The stent retriever of claim 16, wherein the stent retriever comprises a length of between 10 mm and 60 mm.

\* \* \* \* \*